United States Patent [19]

Jarema

[11] Patent Number: 6,028,040
[45] Date of Patent: Feb. 22, 2000

[54] THICKENED NAIL POLISH REMOVER

[75] Inventor: Chester P. Jarema, Sterling Heights, Mich.

[73] Assignee: J. Stephen Scherer, Inc., Rochester Hills, Mich.

[21] Appl. No.: 09/294,944

[22] Filed: Apr. 20, 1999

Related U.S. Application Data

[63] Continuation-in-part of application No. 09/158,275, Sep. 22, 1998, abandoned.
[51] Int. Cl.$^7$ .............................. A61K 7/047; C11D 1/62; C11D 3/37; C11D 3/43
[52] U.S. Cl. .......................... 510/118; 510/403; 510/434; 510/499; 510/476
[58] Field of Search .................................... 510/118, 403, 510/434, 499, 476

[56] References Cited

U.S. PATENT DOCUMENTS 5,543,085   8/1996   Miner ...................................... 510/118

OTHER PUBLICATIONS

"Thickening & Suspending with Carbopol Resins", pp. 14, 21, 22, 24–26, and 52 (Apr. 1995).
Hawley's Condensed Chemical Dictionary, p. 318 (1993).
"Thickening and Suspending with Carbopol Resins", B.F. Goodrich Trade Literature, p. 23, Apr. 1995.

*Primary Examiner*—Yogendra Gupta
*Assistant Examiner*—Christine Ingersoll
*Attorney, Agent, or Firm*—MacMillan, Sobanski & Todd, LLC

[57] ABSTRACT

A thickened nail polish remover includes a solvent/water blend containing a major amount of organic solvent and a minor amount of water. The nail polish remover also includes a water-wetted thickener that, when dry, is readily dispersible in water but not readily dispersible in the solvent/water blend. The nail polish remover further includes a long chain amine neutralizing agent. The thickened nail polish remover has a viscosity of from 3,000 centipoise to 90,000 centipoise at 21° C. In one embodiment, the thickened nail polish remover is formulated to be easily rinsable from the nails with water, by selecting a long chain amine neutralizing agent so that the neutralized thickener is compatible both with the solvent/water blend and with the water used to rinse the nails. In the method of preparing the thickened nail polish remover, the thickener is prewetted with the water of the solvent/water blend to form a dispersion of the thickener in the water. The prewetted thickener and water are then mixed with the solvent of the solvent/water blend, and with a long chain amine neutralizing agent, to produce the thickened nail polish remover.

19 Claims, No Drawings

THICKENED NAIL POLISH REMOVER

CROSS-REFERENCE TO RELATED APPLICATION

This application is a continuation-in-part of Ser. No. 09/158,275, filed Sep. 22, 1998, now abandoned.

BACKGROUND OF THE INVENTION

1. Field of the Invention

The present invention relates to a thickened nail polish remover and to a method of preparing the nail polish remover. More specifically, the invention relates to an improved thickened nail polish remover including a solvent/water blend containing a major amount of organic solvent, a water-wetted thickener, and a long chain amine neutralizing agent. The thickener, when dry, is readily dispersible in water but not readily dispersible in the solvent/water blend.

2. Description of Related Art

Products have long been marketed for the removal of nail polish from fingernails and toenails. These products contain a solvent with which to dissolve the nail polish, along with other ingredients. The solvent makes the nail polish remover highly fluid. A highly fluid product has certain disadvantages, such as ease of spillage, smearability, and poor measurability.

Several patents disclose thickened or gelled nail polish removers. For example, U.S. Pat. No. 4,804,486, issued to Day, discloses a cream-like nail polish remover containing a low vapor pressure solvent, a gelling agent, a two-part amine neutralizing system, an antibacterial agent and water. The patent teaches away from the use of a high vapor pressure solvent such as acetone or ethyl acetate. There is no disclosure of a water-wetted thickener that, when dry, is readily dispersible in water but not readily dispersible in a solvent/water blend.

The two different amines are required components of the neutralizing system.

U.S. Pat. No. 5,543,085, issued to Miner, discloses a thickened nail polish remover containing a solvent, a thickener and an electrolyte. The electrolyte is a required component of the nail polish remover. There is no disclosure of a water-wetted thickener that, when dry, is readily dispersible in water but not readily dispersible in a solvent/water blend.

U.S. Pat. No. 4,197,212, issued to Minton et al., discloses a gelled nail polish remover containing acetone or ethyl acetate solvent, and a gelling agent. There is no disclosure of a solvent/water blend, and no disclosure of an amine neutralizing agent. There is no disclosure of a water-wetted thickener as described above.

U.S. Pat. No. 5,024,779, issued to Helioff et al., discloses a thickened nail polish remover containing a solvent, a gelling agent comprising a hydrolyzed and neutralized crosslinked maleic anhydride $C_1$–$C_4$ alkyl vinyl ether copolymer, a neutralizing agent, water and a humectant. The particular gelling agent is a required component of the nail polish remover. There is no disclosure of a water-wetted thickener as described above.

The thickened nail polish removers disclosed in the prior patents are not totally satisfactory in all respects, such as product characteristics and ease of manufacture.

Accordingly, it is an object of the present invention to provide a thickened nail polish remover having desirable product characteristics. A particular object of the present invention is to provide a thickened nail polish remover having very good viscosity and appearance.

Another object of the present invention is to provide a thickened nail polish remover that is easy to manufacture. A particular object of the present invention is to provide a thickened nail polish remover that can be manufactured quickly, without high shear mixing, and with simple equipment.

A further object of the present invention is to provide a thickened nail polish remover that can be easily rinsed from the nails with water.

SUMMARY OF THE INVENTION

The above objects are achieved and shortcomings of the prior art are overcome by the present invention, which relates to a thickened nail polish remover and to a method of preparing the nail polish remover. The nail polish remover includes a solvent/water blend comprising a major amount of organic solvent and a minor amount of water. The nail polish remover also includes a water-wetted thickener that, when dry, is readily dispersible in water but not readily dispersible in the solvent/water blend. The nail polish remover further includes a long chain amine neutralizing agent. The thickened nail polish remover has a viscosity within a range of from about 3,000 centipoise to about 90,000 centipoise at 21° C. In one embodiment, the thickened nail polish remover is formulated to be easily rinsable from the nails with water, by selecting a long chain amine neutralizing agent so that the neutralized thickener is compatible both with the solvent/water blend and with the water used to rinse the nails. In the method of preparing the thickened nail polish remover, the thickener is prewetted with the water of the solvent/water blend to form a dispersion of the thickener in the water. The prewetted thickener and water are then mixed with the solvent of the solvent/water blend, and with a long chain amine neutralizing agent, to produce the thickened nail polish remover.

Further objects, benefits and advantages of the present invention will become apparent to those skilled in the art from the following detailed description of the preferred embodiments.

DETAILED DESCRIPTION OF THE PREFERRED EMBODIMENTS

The thickened nail polish remover of the present invention is based on a solvent/water blend including a major amount of organic solvent and a minor amount of water. Such blends were found to provide the optimum combination of product effectiveness and desirable product characteristics. Suitable organic solvents are known to persons skilled in the art, and include ketones, esters, alcohols, glycol ethers, hydrocarbons, and others. Some examples of preferred organic solvents are acetone, ethyl acetate and methyl acetate. Blends of organic solvents can also be used.

Some organic solvents, such as acetone, are miscible with water. Other organic solvents, such as ethyl acetate and methyl acetate, are essentially immiscible with water. When the solvent is immiscible with water, the thickened nail polish remover preferably includes an alcohol to couple the solvent and water so that they do not separate. Suitable alcohols include, for example, isopropyl alcohol and ethyl alcohol. The thickener helps to prevent separation of the solvent from the water. In one embodiment of the invention, the alcohol is added at a level insufficient to couple the solvent and water without the presence of the thickener, but the presence of the thickener enables the alcohol to couple the organic solvent and the water.

The thickened nail polish remover preferably includes from about 70% to about 95% solvent and from about 5% to about 30% water, by weight of the composition. When an alcohol is added to couple the solvent and water, the composition preferably includes from about 25% to about 85% solvent, from about 10% to about 45% alcohol, and from about 5% to about 30% water, by weight of the composition. Preferred compositions contain from about 15% to about 30% water, to insure that sufficient water is present to wet the thickener, even when relatively large amounts of thickener are used in the composition.

The thickened nail polish remover also includes a thickener that, when dry, is readily dispersible in water but not readily dispersible in the solvent/water blend which contains a major amount of organic solvent. The use of such a thickener in the solvent/water blend is contrary to conventional thinking. However, it was found that the thickener can be incorporated into the composition by prewetting the thickener with the water before adding the solvent and neutralizing agent. By "prewetted" is meant that the thickener is dispersed in sufficient water, for sufficient time, and with sufficient mixing, to insure that substantially all the particles of the thickener are wetted by the water. When the prewetting step is completed, substantially all of the thickener is dispersed in the water, with substantially no solid particles of the thickener remaining undispersed. If necessary, the water can be heated to facilitate the dispersion of the thickener in the water, but then cooled so as not to volatilize the solvent.

The thickener is "readily dispersible" in water, which means that the thickener can be quickly dispersed in water with little or no mixing, and particularly without requiring vigorous mixing such as high shear mixing. The thickener readily disperses to form a uniform distribution of thickener particles in the water. There are no lumps of undispersed thickener present, and no large gel particles formed.

The use of the thickener that is readily dispersible in water allows the thickened nail polish remover to be manufactured quickly and easily. For example, the short mixing time allows the manufacture of a product in under one minute, and sometimes as quickly as 10–15 seconds. The thickener can be dispersed without high shear mixing, thereby saving time and energy, and preventing solvent loss. There is no need for sophisticated equipment such as sealed containers to retain the solvent vapors, because the product is manufactured quickly enough that little, if any, solvent is lost. Preferably, the mixing equipment is set at a low mixing speed to minimize solvent loss. In contrast, the use of a thickener typically used in a solvent/water blend would be significantly slower because the thickener would require high shear mixing and a longer mixing time for dispersion.

While the thickener is readily dispersible in water, the thickener is not readily dispersible in the solvent/water blend containing a major amount of organic solvent. Any type of thickener having these properties is suitable for use in the present invention. In a particular embodiment, the thickener is a polyacrylic acid which has been treated to make it readily dispersible in water, e.g., surface treated after polymerization, and/or treated by changing the chemical structure during polymerization. Some examples of suitable thickeners are the EZ-series and ETD-series CARBOPOL® resins, sold by B. F. Goodrich Specialty Polymers and Chemicals Division, Cleveland, Ohio.

The amount of thickener is usually from about 0.4% to about 5% by weight of the total composition of solvent, water and thickener, and preferably from about 0.4% to about 2%. In some compositions, the amount of thickener as a percentage of the water is greater than 5%.

The thickened nail polish remover also includes a long chain amine neutralizing agent. The thickener is neutralized to completely uncoil the molecules of the thickener and provide effective thickening. The long chain amine neutralizing agent is an amine having at least one long chain alkyl group attached to the nitrogen atom. The long chain alkyl group has at least 8 carbon atoms, and can be straight chain or branched chain. Some examples of suitable long chain amine neutralizing agents are di-2-ethylhexylamine, sold by BASF Wyandotte Corp., and ethoxylated polyoxyethylene cocamine, sold under the trademark ETHOMEEN C-25 by Akzo Nobel Chemicals, Inc.

The resulting thickened nail polish remover has a viscosity within a range of from about 3,000 centipoise to about 90,000 centipoise at 21° C., preferably from about 5,000 centipoise to about 70,000 centipoise, more preferably from about 7,000 centipoise to about 50,000 centipoise, and most preferably from about 10,000 centipoise to about 35,000 centipoise. The viscosity of the thickened nail polish remover is measured with a Brookfield viscometer. The product is stable so that it does not lose its viscosity over time. This is important in a product that may be stored on a shelf for a year or longer. The product also has excellent clarity.

Advantageously, the thickened nail polish remover can be the same formulation as a currently marketed product, except that the thickener and neutralizing agent are added to make a thickened or gelled product. Consumers have recently shown a preference for various types of gelled products.

Preferably, the thickened nail polish remover is non-thixotropic to enhance control of the flow of the nail polish remover. "Non-thixotropic" is defined as the characteristic that enables the nail polish remover to immediately recover its viscosity after stress is applied and removed, such as, for example, during application of the nail polish remover. This contrasts with a thixotropic nail polish remover which takes some time to recover its viscosity after stress is applied, and as a result may become undesirably fluid.

In a preferred embodiment of the invention, the thickened nail polish remover has short flow rheology, which is characterized as a gelled consistency similar to mayonnaise. Long flow rheology, on the other hand, is characterized as a consistency similar to honey.

In another embodiment of the invention, the thickened nail polish remover is formulated to be easily rinsable from the nails with water. It has been found that the key to providing an easily rinsable, thickened nail polish remover is the selection of the long chain amine neutralizing agent for the thickener. The amine is selected so that the amine-neutralized thickener is compatible both with the solvent/water blend of the nail polish remover and with the water used to rinse the nails. When the solvent is acetone, the use of either di-2-ethylhexylamine or ethoxylated polyoxyethylene cocamine as the neutralizing agent produces an easily rinsable product. When the solvent is ethyl acetate, the use of ethoxylated polyoxyethylene cocamine as the neutralizing agent produces an easily rinsable product, while using di-2-ethylhexylamine produces a product that is more difficult to rinse.

The thickened nail polish remover of the present invention provides many additional advantages, including the following:

Spillproof, protecting clothes from stains.

Easily applied, in an easily measured amount, conserving product.

Removable without smearing.

Subject to a lower evaporation rate, thereby producing less odor.

Capable of greater efficacy in polish removal, thereby requiring less product to remove the polish.

In a preferred embodiment of the invention, the thickened nail polish remover is applied from a squeeze-type container, e.g., a plastic container with a spout on top having a small opening for dispensing the product, similar to a VISINE® container. When the thickened nail polish remover is stored in a squeeze-type container, preferably the product has a viscosity in the low end of the range described above, to insure easy dispensing. A lower viscosity product also dries faster.

In a particular embodiment of the invention, the thickened nail polish remover has a plurality of gas bubbles suspended therein. This product can be manufactured by mixing the components at high speed to incorporate air bubbles into the product. A surfactant may also be added to the product to facilitate the suspension of the gas bubbles. The thickened nail polish remover with suspended gas bubbles has a unique and attractive appearance.

A preferred thickened nail polish remover using acetone as the solvent includes the following ranges of components:

| Component | Weight % |
| --- | --- |
| Acetone | 75%–85% |
| Water | 15%–25% |
| Polyacrylic acid thickener | 0.4%–1.0% |
| Di-2-ethylhexylamine | 1.1%–2.5% |

A preferred thickened nail polish remover using ethyl acetate as the solvent includes the following ranges of components:

| Component | Weight % |
| --- | --- |
| Ethyl acetate | 55%–65% |
| Water | 15%–25% |
| Alcohol | 20%–30% |
| Polyacrylic acid thickener | 0.4%–1.0% |
| Ethoxylated polyoxyethylene cocamine | 1.1%–6.1% |

The thickened nail polish remover can optionally include additives such as perfumes, emollients, conditioning agents, opacifiers, antioxidants, antibacterial agents, humectants, and colorants. In a preferred embodiment, the thickened nail polish remover does not include an electrolyte.

EXAMPLE 1

This example demonstrates the effect of prewetting the thickener in making a thickened nail polish remover with a solvent/water blend. Samples of nail polish remover using acetone as the solvent were prepared as follows:

| Component | Weight (g) |
| --- | --- |
| Acetone | 80 |
| Water | 20 |
| Thickener (Carbopol EZ-2) | 1.0 |
| Neutralizing agent (di-2-ethylhexylamine) | 1.0 |

In a first sample, the acetone and water were mixed together, and then the thickener was added and mixed, and the neutralizing agent was added and mixed. The thickener did not disperse in the acetone/water blend; the product contained undispersed solid particles of the thickener. In a second sample, the thickener was dispersed in the water with stirring and allowed to sit for about 10 minutes until the thickener became completely prewetted. Then the acetone was added and mixed, and the neutralizing agent was added and mixed. The resulting product was a thick, homogenous gel.

Samples of nail polish remover using ethyl acetate as the solvent were prepared as follows:

| Component | Weight (g) |
| --- | --- |
| Ethyl acetate | 60 |
| Water | 17.5 |
| Isopropyl alcohol | 22.5 |
| Thickener (Carbopol EZ-2) | 1.5 |
| Neutralizing agent (di-2-ethylhexylamine) | 3.0 |

In a first sample, the ethyl acetate, isopropyl alcohol and water were mixed together, and then the thickener was added and mixed, and then the neutralizing agent was added and mixed. The thickener did not disperse in the ethyl acetate/isopropyl alcohol/water blend; the product contained undispersed solid particles of the thickener. In a second sample, the thickener was dispersed in the water with stirring and allowed to sit for about 10 minutes until the thickener became completely prewetted. Then the ethyl acetate and isopropyl alcohol were added and mixed, and the neutralizing agent was added and mixed. The resulting product was a thick, homogenous gel.

EXAMPLE 2

This example demonstrates the effect on viscosity of varying the amounts of thickener and neutralizing agent in the thickened nail polish remover. A series of nail polish remover samples were prepared from acetone, water, Carbopol EZ-2 thickener and di-2-ethylhexylamine neutralizing agent. The thickener was prewetted by dispersion in the water with stirring. Then the acetone was added and mixed, and the neutralizing agent was added and mixed. The following results were obtained:

| Acetone | Water | Carbopol EZ-2 | Di-2-ethyl-hexylamine | Viscosity (after 1 day) |
| --- | --- | --- | --- | --- |
| 80 g | 20 g | 1.0 g | 1.0 g | 40,500 cps |
| 80 g | 20 g | 1.0 g | 0.75 g | 39,500 cps |
| 80 g | 20 g | 1.0 g | 0.5 g | 38,000 cps |
| 80 g | 20 g | 1.0 g | 0.25 g | 27,500 cps |

-continued

| Acetone | Water | Carbopol EZ-2 | Di-2-ethyl-hexylamine | Viscosity (after 1 day) |
|---|---|---|---|---|
| 80 g | 20 g | 0.75 g | 0.25 g | 24,000 cps |
| 80 g | 20 g | 0.50 g | 0.25 g | 15,500 cps |
| 80 g | 20 g | 0.35 g | 0.25 g | 9,000 cps |
| 80 g | 20 g | 0.325 g | 0.25 g | 7,500 cps |
| 80 g | 20 g | 0.30 g | 0.25 g | 6,500 cps |
| 80 g | 20 g | 0.25 g | 0.25 g | 3,500 cps |

The results show that the viscosity of the thickened nail polish remover is affected by both the amount of thickener and the amount of neutralizing agent in the composition.

EXAMPLE 3

This example demonstrates the effects of the alcohol and the thickener in preventing separation of the organic solvent from the water in the thickened nail polish remover. A series of compositions were prepared from ethyl acetate, water, and alcohol, and without a thickener. The amounts of water and alcohol were varied to determine the minimum amount of alcohol necessary to couple the ethyl acetate to the water without a thickener. In a first group of the compositions, the alcohol was isopropyl alcohol, and in a second group, the alcohol was ethyl alcohol. The compositions were prepared by mixing together the ethyl acetate and alcohol, and then mixing in the water. The following results were obtained:

| Ethyl Acetate | Isopropyl Alcohol | Ethyl Alcohol | Water | Result |
|---|---|---|---|---|
| 60 g | 25 g | | 15 g | Coupling |
| 60 g | 22.5 g | | 17.5 g | Coupling |
| 60 g | 20 g | | 20 g | Separation |
| 60 g | 15 g | | 25 g | Separation |
| 60 g | | 20 g | 20 g | Coupling |
| 60 g | | 17.5 g | 22.5 g | Separation |
| 60 g | | 15 g | 25 g | Separation |

The results show that in the compositions made without a thickener, at least about 22.5% isopropyl alcohol or at least about 20% ethyl alcohol is needed to couple the ethyl acetate to the water. In the compositions made with less alcohol, the ethyl acetate and water separated into upper and lower layers.

It was decided that the addition of the thickener might help to prevent separation of the ethyl acetate from the water. Two of the compositions in which separation occurred were prepared again, except that the compositions were thickened by the addition of a thickener and a neutralizing agent. Specifically, the first thickened composition contained 60 grams of ethyl acetate, 15 grams of isopropyl alcohol, 25 grams of water, 1.25 grams of Carbopol EZ-2 thickener, and 3.0 grams of di-2-ethylhexylamine neutralizing agent. The thickener was dispersed in the water, and then the ethyl acetate and isopropyl alcohol were added and mixed, and then the neutralizing agent was added and mixed. The water/thickener remained as a lower layer separate from the ethyl acetate/isopropyl alcohol. Apparently, there was not enough isopropyl alcohol present to couple the ethyl acetate and water, even with the addition of the thickener.

The second thickened composition contained 60 grams of ethyl acetate, 20 grams of isopropyl alcohol, 20 grams of water, 1.30 grams of the thickener, and 3.0 grams of the neutralizing agent. The thickener was dispersed in the water, and then the ethyl acetate and isopropyl alcohol were added and mixed, and then the neutralizing agent was added and mixed. Surprisingly, the water/thickener formed a homogenous gel with the ethyl acetate/isopropyl alcohol. There was no separation of the water from the alcohol. The resulting thickened nail polish remover had a viscosity of about 30,000 centipoise.

EXAMPLE 4

This example demonstrates the use of different amounts of solvent and water in the thickened nail polish remover. A first sample of a thickened nail polish remover was prepared as follows:

| Component | Weight (g) |
|---|---|
| Acetone | 80 |
| Water | 20 |
| Thickener (Carbopol EZ-2) | 0.75 |
| Neutralizing agent (di-2-ethylhexylamine) | 0.25 |

The water was poured into a beaker. Then, the thickener was added to the water in the beaker and allowed to sit for 10 minutes. During this time, the thickener was completely wetted by the water. The acetone was added to the beaker and stirred to produce a uniform dispersion. The neutralizing agent was added to the beaker and stirred for 30–60 seconds. A clear, thickened nail polish remover was produced, having a viscosity of 24,000 centipoise after one day.

A second sample of a thickened nail polish remover was prepared as follows:

| Component | Weight (g) |
|---|---|
| Acetone | 85 |
| Water | 15 |
| Thickener (Carbopol EZ-2) | 1.0 |
| Neutralizing agent (di-2-ethylhexylamine) | 1.0 |

The same procedure as described above was followed, except that the water was allowed to wet the thickener for 25 minutes instead of 10 minutes, because the lower amount of water takes more time to wet the thickener. A clear, thickened nail polish remover was produced, having a viscosity of 25,000 centipoise after three days.

EXAMPLE 5

This example demonstrates the preparation of a first thickened nail polish remover which is difficult to rinse with water, and a second thickened nail polish remover which is easy to rinse with water. The first thickened nail polish remover was prepared from the following components:

| Component | Weight (g) |
|---|---|
| Ethyl acetate | 60 |
| Water | 17.5 |
| Isopropyl alcohol | 22.5 |

-continued

| Component | Weight (g) |
|---|---|
| Thickener (Carbopol EZ-2) | 1.5 |
| Di-2-ethylhexylamine | 3.0 |

The water and thickener were weighed into a beaker and stirred. Then a mixture of the ethyl acetate and isopropyl alcohol was poured into the beaker and stirred. The di-2-ethylhexylamine was then weighed into the beaker and stirred. A thickened nail polish remover resulted, having a viscosity of 36,000 centipoise. However, when the beaker which contained the nail polish remover was cleaned with water, it was found to be difficult to clean. The nail polish remover left a gummy, sticky residue in the beaker. It is believed that this residue was caused by the amine-neutralized thickener (thickener/di-2-ethylhexylamine) which was not compatible with water.

The second thickened nail polish remover was prepared as described above, except that neutralizing agent used was 6.0 grams of ethoxylated polyoxyethylene cocamine (Ethomeen C-25) instead of 3.0 grams of di-2-ethylhexylamine. Also, the composition included 1.0 gram of the thickener instead of 1.5 grams. The resulting thickened nail polish remover had a viscosity of 18,000 centipoise. The product was easily rinsable with water, unlike the first product, because the amine-neutralized thickener (thickener/ethoxylated polyoxyethylene cocamine) was compatible with water.

The principle and mode of operation of this invention have been described in its preferred embodiments. However, it should be noted that this invention may be practiced otherwise than as specifically illustrated and described without departing from its scope.

What is claimed is:

1. A thickened nail polish remover based on a solvent/water blend, comprising:
   a solvent/water blend comprising a major amount of organic solvent and a minor amount of water;
   a water-wetted thickener that, when dry, is readily dispersible in water but not readily dispersible in the solvent/water blend; and
   a long chain amine neutralizing agent;
   the thickened nail polish remover having a viscosity within a range of from about 3,000 centipoise to about 90,000 centipoise at 21° C.; and
   the thickened nail polish remover containing no electrolyte.

2. The thickened nail polish remover defined in claim 1 wherein the thickened nail polish remover is non-thixotropic.

3. The thickened nail polish remover defined in claim 1 wherein the thickener is a polyacrylic acid.

4. The thickened nail polish remover defined in claim 1 wherein the solvent/water blend comprises from about 70% to about 95% organic solvent and from about 5% to about 30% water by weight of the composition.

5. The thickened nail polish remover defined in claim 1 wherein the thickened nail polish remover comprises greater than 5% thickener by weight of the water.

6. The thickened nail polish remover defined in claim 1 wherein the neutralizing agent is selected from the group consisting of di-2-ethylhexylamine and ethoxylated polyoxyethylene cocamine.

7. The thickened nail polish remover defined in claim 1 wherein the organic solvent is acetone.

8. The thickened nail polish remover defined in claim 1 wherein the organic solvent is selected from the group consisting of ethyl acetate, methyl acetate, and mixtures thereof, and wherein the thickened nail polish remover additionally comprises an alcohol to couple the organic solvent to the water.

9. The thickened nail polish remover defined in claim 8 wherein the thickener prevents separation of the organic solvent from the water.

10. A thickened nail polish remover wherein the thickened nail polish remover comprises from about 75% to about 85% acetone, from about 15% to about 25% water, from about 0.4% to about 1.0% polyacrylic acid thickener, and from about 1.1% to about 2.5% di-2-ethylhexylamine, by weight.

11. A thickened nail polish remover wherein the thickened nail polish remover comprises, by weight, from about 55% to about 65% ethyl acetate, from about 15% to about 25% water, from about 20% to about 30% isopropyl alcohol, from about 0.4% to about 1.0% polyacrylic acid thickener, and from about 1.1% to about 6.1% of a long chain amine neutralizing agent selected from the group consisting of ethoxylated polyoxyethylene cocamine and di-2-ethylhexylamine.

12. A thickened nail polish remover based on a solvent/water blend, comprising:
    a solvent/water blend comprising a major amount of organic solvent and a minor amount of water;
    a water-wetted thickener that, when dry, is readily dispersible in water but not readily dispersible in the solvent/water blend; and
    a long chain amine neutralizing agent;
    the thickened nail polish remover having a viscosity within a range of from about 3,000 centipoise to about 90,000 centipoise at 21° C. additionally compromising a plurality of gas bubbles suspended in the thickened nail polish remover, the viscosity of the thickened nail polish remover enabling the gas bubbles to remain suspended.

13. A method of preparing a thickened nail polish remover based on a solvent/water blend, the method comprising:
    providing a thickener that, when dry, is readily dispersible in water but not readily dispersible in a solvent/water blend comprising a major amount of organic solvent and a minor amount of water;
    prewetting the thickener with the water of the solvent/water blend to form a dispersion of the thickener in the water; and
    mixing the prewetted thickener and the water with the solvent of the solvent/water blend, and with a long chain amine neutralizing agent, to produce a thickened nail polish remover having a viscosity within a range of from about 3,000 centipoise to about 90,000 centipoise at 21° C. the thickened nail polish remover containing no electrolyte.

14. The method defined in claim 13 wherein the thickened nail polish remover which is produced is non-thixotropic.

15. The method defined in claim 13 wherein the thickened nail polish remover which is produced has short flow rheology.

16. The method defined in claim 13 wherein the thickener which is provided is a polyacrylic acid.

17. A thickened nail polish remover based on a solvent/water blend, the thickened nail polish remover being easily rinsable from the nails with water, comprising:

a solvent/water blend comprising a major amount of organic solvent and a minor amount of water;

a water-wetted thickener that, when dry, is readily dispersible in water but not readily dispersible in the solvent/water blend; and a long chain amine which neutralizes the thickener;

wherein the long chain amine is selected so that the neutralized thickener is compatible both with the solvent/water blend and with the water used to rinse the nails;

the thickened nail polish remover having a viscosity within a range of from about 3,000 centipoise to about 90,000 centipoise at 21° C. the thickened nail polish remover containing no electrolyte.

18. The thickened nail polish remover defined in claim 17 wherein the long chain amine is ethoxylated polyoxyethylene cocamine.

19. The nail polish remover defined in claim 17 wherein the thickener is a polyacrylic acid.

* * * * *